US010940302B2

(12) United States Patent
Achard de la Vente

(10) Patent No.: US 10,940,302 B2
(45) Date of Patent: Mar. 9, 2021

(54) IMPLANTABLE ACCESS DEVICE FOR ACCESSING THE VASCULAR SYSTEM OF A HUMAN OR ANIMAL BODY

(71) Applicant: PFM MEDICAL AG, Cologne (DE)

(72) Inventor: Stanislas Marie Bertrand Achard de la Vente, Canton de Neuchatel (CH)

(73) Assignee: PFM MEDICAL AG, Cologne (DE)

( * ) Notice: Subject to any disclaimer, the term of this patent is extended or adjusted under 35 U.S.C. 154(b) by 98 days.

(21) Appl. No.: 15/939,976

(22) Filed: Mar. 29, 2018

(65) Prior Publication Data

US 2018/0280676 A1 Oct. 4, 2018

(30) Foreign Application Priority Data

Mar. 30, 2017 (EP) .................................... 17163808

(51) Int. Cl.
*A61M 39/02* (2006.01)
*A61M 25/00* (2006.01)
*A61M 39/00* (2006.01)

(52) U.S. Cl.
CPC .... *A61M 39/0247* (2013.01); *A61M 25/0097* (2013.01); *A61M 39/0208* (2013.01);
(Continued)

(58) Field of Classification Search
CPC ... F16K 7/04; F16K 7/06; F16K 7/066; A61B 17/3498; A61M 39/0247; A61M 39/0208;
(Continued)

(56) References Cited

U.S. PATENT DOCUMENTS 4,861,341 A    8/1989  Woodburn
5,350,360 A    9/1994  Ensminger et al.
(Continued)

FOREIGN PATENT DOCUMENTS

DE    19624320    10/1997
EP    0332943    9/1989
(Continued)

*Primary Examiner* — Kami A Bosworth
*Assistant Examiner* — Antarius S Daniel
(74) *Attorney, Agent, or Firm* — Grossman, Tucker, Perreault & Pfleger, PLLC

(57) ABSTRACT

The invention relates to an implantable access device for accessing the vascular system of a human or animal body, particularly subcutaneously implantable access port, comprising: at least one inlet opening, at least one outlet opening and at least one passageway between the at least one inlet opening and the at least one outlet opening, further comprising at least one valve assembly in the at least one passageway, which in a first, unactuated operating condition prevents a fluid flow through the at least one passageway and in a second, actuated operating condition permits a fluid flow through the at least one passageway, which is characterized in that the at least one valve assembly in the first, unactuated operating condition is longitudinally elongated and radially compressed in such a way to prevent a fluid flow through the at least one passageway and that the at least one valve assembly in the second, actuated operating condition is longitudinally compressed and radially elongated in such a way to permit a fluid flow through the at least one passageway.

19 Claims, 5 Drawing Sheets

(52) U.S. Cl.
CPC ............... *A61M 2039/0036* (2013.01); *A61M 2039/027* (2013.01); *A61M 2039/0258* (2013.01); *A61M 2039/0276* (2013.01); *A61M 2039/0282* (2013.01); *A61M 2210/125* (2013.01)

(58) Field of Classification Search
CPC ...... A61M 39/0226; A61M 2039/0258; A61M 2039/027; A61M 2039/0282; A61M 2039/0276; A61M 2039/0223; A61M 2039/0244; A61M 2039/1027; A61M 2039/1061; A61M 39/22; A61M 39/26; A61M 39/28; A61M 39/06; A61M 2039/0294; A61M 2039/263
See application file for complete search history.

(56) References Cited

U.S. PATENT DOCUMENTS

| | | | |
|---|---|---|---|
| 5,352,204 | A | 10/1994 | Ensminger |
| 5,356,381 | A | 10/1994 | Ensminger et al. |
| 5,741,228 | A | 4/1998 | Lambrecht et al. |
| 5,810,323 | A * | 9/1998 | Winterer ............. A61M 39/286 251/4 |
| 5,848,989 | A | 12/1998 | Villani |
| 5,911,706 | A | 6/1999 | Estabrook et al. |
| 6,007,516 | A | 12/1999 | Burbank et al. |
| 6,056,717 | A | 5/2000 | Finch et al. |
| 6,120,492 | A | 9/2000 | Finch et al. |
| 6,193,684 | B1 | 2/2001 | Burbank et al. |
| 6,206,851 | B1 * | 3/2001 | Prosl ................. A61M 39/0208 604/256 |
| 6,506,182 | B2 | 1/2003 | Estabrook et al. |
| 6,565,525 | B1 | 5/2003 | Burbank et al. |
| 7,056,316 | B1 | 6/2006 | Burbank et al. |

FOREIGN PATENT DOCUMENTS

| | | |
|---|---|---|
| EP | 1016431 | 7/2000 |
| EP | 1629862 | 3/2006 |
| EP | 1765456 | 11/2011 |

* cited by examiner

IMPLANTABLE ACCESS DEVICE FOR ACCESSING THE VASCULAR SYSTEM OF A HUMAN OR ANIMAL BODY

FIELD

The invention relates to an implantable access device for accessing the vascular system of a human or animal body, particularly subcutaneously implantable access port.

BACKGROUND

During a medical treatment it is sometimes necessary to repeatedly access the vascular system of a human or animal body, for example for infusing therapeutic agents, drugs or such the like, removing body fluids, treating body fluids, injecting contrast agents and/or insertion of medical devices such as cameras, ultra-sound probes, brushes, catheters, catching devices or similar devices. In case of fluid exchange therapies, like for example hemodialysis, hemofiltration, hemodiafiltration, plasmapheresis, ultrafiltration, aquafiltration, n lipid pheresis, hemoperfusion, peritoneal dialysis or the like, devices for accessing the vascular system of a human or animal body which allow a high-volume fluid flow are preferred.

From the prior art a variety of strategies are known for accessing the vascular system of a human or animal body, like for example direct vessel cannulation, short and long term catherization and implantation of subcutaneous port systems.

A temporary access to the vascular system of the human or animal body can be simply provided by a direct percutaneous introduction of a needle through the skin of the human or animal body into a vessel of the vascular system of the human or animal body. Such an approach is the least expensive and simplest form of accessing the vascular system of the human or animal body and is particularly suitable for short term applications like for example intravenous drug delivery, removal of blood or the like. However, repeated introduction of a needle through the skin of the human or animal body into a vessel of the vascular system of the human or animal body can result in vessel thrombosis, stenosis and formation of pseudo-aneurisms, as well as infections.

Transcutaneous devices, like short and long term catheters, are used to address the problems of repeated direct percutaneous introduction of a needle through the skin of the human or animal body into a vessel of the vascular system of the human or animal body. Such transcutaneous devices can be flexible cannulae, which are inserted percutaneously into the region of interest such as a blood vessel or cavity in the human or animal body. However, although transcutaneous devices deal with the problems of a direct percutaneous introduction of a needle through the skin of the human or animal body into a vessel of the vascular system of the human or animal body they often cause complications due to infections. The infection usually infects the point where the device passes through the skin of the human or animal body or even the vascular system of the human or animal body itself. Thus, such transcutaneous devices can cause local or even systemic infections.

Therefore a direct percutaneous introduction of a needle through the skin of the human or animal body into a vessel of the vascular system of the human or animal body or use of a transcutaneous catheter are not well suited for long term applications or for extracorporeal procedures that must be repeated periodically, like for example hemodialysis, hemofiltration, hemodiafiltration, plasmapheresis, ultrafiltration, aquafiltration, n lipid pheresis, hemoperfusion, peritoneal dialysis or the like.

To deal with the above problems varieties of subcutaneously implanted ports have been proposed over the years for long term and/or periodically repeated accesses to the vascular system of the human or animal body. A typical subcutaneously implanted port has an access region for receiving a needle or access catheter, a fluid flow path through the port and a subcutaneously catheter attached to a vessel of the vascular system of the human or animal body. Thus, a fluid flow path is provided from the access catheter through the subcutaneously implanted port and the subcutaneously catheter to the vascular system of the human or animal body.

The most common type of subcutaneously implanted ports, like for example disclosed in U.S. Pat. No. 6,056,717, comprises a housing with a port chamber for receiving an introduced needle. The surface of the port chamber next to the skin of the human or animal body is enclosed by a high-density self-sealing septum, typically made of silicone rubber. A subcutaneously implanted catheter, which communicates with a vein or other site within the human or animal body, is connected and in fluid connection to the port chamber. Implantation of such devices generally proceeds by making a small subcutaneous pocket in an appropriate area of the human or animal body under local anesthesia. The subcutaneously implanted catheter is tunneled to the desired infusion site.

Since the septum faces towards the skin of the human or animal body and the subcutaneously implanted catheter runs substantially parallel to the skin of the human or animal body, there exists a 90° bend in the flow path from the introduced needle, which is perpendicular to the skin of the human or animal body, to the subcutaneously implanted catheter. Especially for high flowrates this can result in damages to the blood, so-called hemolysis.

To avoid damaging or coring of the septum a special needle, like so-called port or Huber needle, is introduced through the skin of the human or animal body and the septum into the port chamber. Damaging or coring of the septum is avoided by a special cut of the needle. After the medical treatment has been finished the needle is withdrawn from the port chamber.

Since large diameter needles can damage the rubber septum used for sealing the port chamber the fluid flow rate is limited for these known subcutaneously implanted port devices. Further, it is desirable to limit the height of the subcutaneously implanted port because for optical reason and the local stress imposed on the skin of the human or animal body. However, this results in a limited height of the port chamber and a small displacement of the introduced needle can cause a retraction of the needle out of the port chamber. In case where toxic materials are being infused, like during chemotherapy, the retraction of the needle out of the port chamber can cause local tissue damage, which may lead to further surgical treatments like corrective surgery or removal of tissue.

Moreover, due to the at least one 90° bend in the fluid flowing path it is difficult or even impossible to clear the subcutaneously implanted port if e.g. thrombosis occurs. A thrombus can result in serious patient injuries like e.g. pulmonary embolism or even blockage. To clear a subcutaneously implanted port it is necessary to feed a cleaning wire through the hypodermic needle into the port chamber and further through the subcutaneously implanted catheter. However, it is very difficult to feed the cleaning wire from the port chamber into the subcutaneously implanted port due to the at least one 90° bend. In case the subcutaneously implanted port cannot be cleaned it has to be replaced to avoid the risk of serious patient injuries.

To overcome the problems associated with the perpendicular introduction of the needle into the port chamber it has been proposed for example in DE 196 24 320 C1, EP 0 332 943 81, EP 1 629 862 A1, EP 1 765 456 81, U.S. Pat. No. 5,848,989 or U.S. Pat. No. 4,861,341 to use a tube shaped subcutaneously implanted port, wherein the septum is arranged in such a way that the needle is introduced substantially parallel to the skin of the human or animal body. This result in a substantially straight fluid flowing path through the subcutaneously implanted port. Due to the substantially straight fluid flowing path a cleaning wire or another device can be easily introduced through the port chamber into the subcutaneously implanted catheter. Further, the length of the catheter housing can be enhanced without causing more stress to the skin in the area of the implantation site. Thus, the length of the port chamber can be enhanced, and the needle can be introduced further into the port chamber and thereby significantly reducing the risk of an accidental retraction of the needle out of the port chamber.

Further, it is known from the prior art, like example from U.S. Pat. No. 6,007,516, U.S. Pat. No. 6,120,492 U.S. Pat. No. 6,193,684 B1 and U.S. Pat. No. 7,056,316 B1, to replace the septum by a valve assembly. Due to the valve assembly fistula needles can be introduced into the subcutaneously implanted port without damaging any septum. Usually the valve is actuated by moving a part of the valve by the introduced needle or by advancing the introduced needle through the valve, like e.g. through a leaflet valve assembly. This even allows use of larger diameter needles, which increases the maximum achievable fluid flowing rate. U.S. Pat. No. 6,565,525 B1 further discloses a dual port vascular access assembly comprising first and second access ports. This vascular access assembly is designed to close the second access port in the absence of an access tube in the first access port. Thus, blood withdrawal will be automatically terminated upon cessation of blood returned to due to loss of the return access tube in the first access port. However, according to the aforementioned prior art documents the needles are introduced perpendicular to the skin of the human or animal body and thus, they still suffer from the above mentioned problems associated with the perpendicular introduction of the needle into the port chamber.

U.S. Pat. No. 5,350,360, EP 1 016 431 A1, U.S. Pat. No. 5,741,228, U.S. Pat. No. 5,356,381 and U.S. Pat. No. 5,352,204 each disclose a subcutaneously implantable access port with a housing having a funnel shaped inlet orifice leading to a reduced diameter guide passageway. An articulating valve, which may take various forms including leaflet type valves or self-collapsing tubular valves, are placed in line with the access port housing. An external filament such as a needle, guide wire, optical fiber, or external catheter can be introduced into the access device and fed through the housing to penetrate the articulating valve.

U.S. Pat. No. 5,911,706 and U.S. Pat. No. 6,506,182 B2 each disclose an implantable single or dual-lumen device for repeated accessing vessels within a human or animal body. The device uses a resilient material to form a seal, and has a smooth streamlined flowpath with no flow discontinuity. The device is joined to a subcutaneously implanted catheter, such that fluids can be extracted from or injected into the vessel to be accessed. The device is designed for the high flowrates, on the order of 150 and greater milliliters per minute, associated with fluid exchange therapies. A smooth flow streaming is important to minimize damage to the blood. A corresponding straight-needle apparatus is designed to mate and lock with the access device, where alignment and open flowpath is ensured. A valve seal incorporates opposing very hard surfaced guide elements that are retained and in intimate contact with the seal itself. The needle assembly pushes open these guide elements which open the seal before the needle point reaches the seal material.

The aforementioned implantable devices with a streamlined flowpath and a valve configuration have the disadvantage that the introduced needle penetrates the valve and thereby damaging the valve. To overcome this problem the prior art suggests to use opposing very hard surfaced guide elements that are retained and in intimate contact with the seal itself.

SUMMARY

It is an object of the present application to provide an implantable device with a streamlined flowpath and a valve configuration, which is suitable for high flowrates associated with fluid exchange therapies and which is easy to manufacture and which minimizes the risk of damages caused by the introduced needle.

This object is solved by an implantable access device for accessing the vascular system of a human or animal body, particularly subcutaneously implantable access port, comprising:
at least one inlet opening, at least one outlet opening and at least one passageway between the at least one inlet opening and the at least one outlet opening,
further comprising at least one valve assembly in the at least one passageway, which in a first, unactuated operating condition prevents a fluid flow through the at least one passageway and in a second, actuated operating condition permits a fluid flow through the at least one passageway,
which is characterized in that
the at least one valve assembly in the first, unactuated operating condition is longitudinally elongated and radially compressed in such a way to prevent a fluid flow through the at least one passageway and that the at least one valve assembly in the second, actuated operating condition is longitudinally compressed and radially elongated in such a way to permit a fluid flow through the at least one passageway.

According to the invention the terms 'elongated' and 'compressed' refer to the difference between the longitudinal or radial dimension in the first and second operating condition respectively. Further, according to the invention the change between the radial elongation and the radial compression does not have to take place around the whole circumference of the at least one passageway to permit respectively prevent the fluid flow through the at least one passageway. In fact, a radial elongation or radial compression taking place only in part of the circumference of the at least one passageway is sufficient to permit respectively prevent the fluid flow through the at least one passageway. On the other hand, the radial elongation or radial compression can take place around the whole circumference of the at least one passageway.

The implantable access device according to the invention is very easy to manufacture since the at least one valve assembly does not need any movable sealing parts or leaflet elements, which are complicated to dimension and manufacture. The valve assembly of the implantable access device according to the invention only changes its longitudinal and radial dimensions from the first, unactuated operating condition to the second, actuated operating condition to open the flowpath through the streamlined passageway between the at least one inlet opening and the at least one outlet opening. By radially elongating the at least one valve assembly in the second, actuated operating condition the passageway is opened. The radial elongation is compensated by the longitudinal compression of the at least one valve assembly in the second, actuated operating condition.

Since the valve assembly radially expands in the second, actuated operating condition the sealing portions of the at least one valve assembly move radially outwards and thus away from the at least one passageway between the at least one inlet opening and the at least one outlet opening. Thus, even if a needle is introduced into the at least one passageway between the at least one inlet opening and the at least one outlet opening the sealing portions of the at least one valve assembly have moved out of the at least one passageway due to the radially outward movement. Thereby the risk of damaging the at least one valve assembly is significantly reduced.

A further advantage of the valve assembly of the implantable access device according to the invention is that during the removal of the needle from the implantable access device a positive pressure is created inside the at least one passageway by the radial compression of the valve assembly. This positive pressure avoids that blood is sucked into the tip of the subcutaneously implanted catheter. if blood is sucked into the subcutaneously implanted catheter after rinsing, this blood can clot for example at the tip of the subcutaneously implanted catheter, which may lead to thrombus that can block the subcutaneously implanted catheter or which can even enter the vascular system of the human or animal body, which might be dangerous to the life of the patient.

In a preferred variant of the invention the at least one valve assembly is arranged in the at least one passageway in such a way, that the at least one valve assembly is actuated by a needle inserted into the at least one inlet opening. Preferably the at least one valve assembly is arranged in the at least one passageway close to the inlet opening. Thus, by inserting the needle into the at least one inlet opening the valve assembly is actuated and the at least one valve assembly changes its operating condition from the first, unactuated operating condition to the second, actuated operating condition.

Alternatively, the at least one valve assembly could also be actuated by manually applying a force through the skin of the human or animal body to a special actuator, like a lever or button at the outside of the housing of the implantable access device, which is located on a surface directed towards the skin of the human or animal body. Further, the at least one valve assembly could also be electronically actuated by transmitting a radio signal to a receiver of the implantable access device or by transmitting electrical energy to the implantable access device to feed power to a special actuator element of the at least one valve assembly.

According to a further variant of the invention the at least one valve assembly comprises at least one spring element to constrain the at least one valve assembly into the first, unactuated operating condition. Thereby it is guaranteed that the at least one valve assembly is always in the first, unactuated operating condition unless it is actually actuated. This avoids any leakage from the at least one inlet opening to the at least one outlet opening or vice versa, which is important for the safety of the patient. A spring element is preferably because it is easy to manufacture and therefore cheap. Further, such a spring element can easily be manufactured from a biocompatible material.

Further, at least a part of the at least one spring element can be located outside of the at least one passageway, so that this part of the at least one spring element does not get into contact with the fluid flowing through the at least one passageway. Preferably the whole at least one spring element is located outside of the at least one passageway, so that the total at least one spring element does not get into contact with the fluid flowing through the at least one passageway. This has the advantage that the fluid flowing through the at least one passageway does not negatively influence the functionality of the at least one spring element. Thus, a malfunction of the at least one spring element caused by a contact with the fluid flowing through the at least one passageway is significantly reduced or even eliminated.

For example, the at least one spring element can extend in a radial direction away from the at least one passageway. In the first, unactuated operating condition the spring element applies a radially inward force on the at least one passageway, which can be e.g. a flexible tube. Once a force is applied to the at least one assembly, particularly to the at least one spring element of the at least one valve assembly, the at least one spring element moves radially outwardly and thus withdraws the radially inward force on the at least one passageway, e.g. the flexible tube, which is thereby opened. Thus, the at least one spring element can implement the two different operating conditions of the at least one valve assembly.

In a variant of the invention the implantable device further comprises at least one needle receptacle arranged in the at least one passageway for receiving a needle inserted into the at least one inlet opening, wherein the needle receptacle preferably prevents a passage of the needle through the needle receptacle. Preferably the at least one needle receptacle is located between the at least one inlet opening of the implantable access device and the at least one valve assembly. The at least one needle receptacle has an inner open diameter, which is part of the at least one passageway between the at least one inlet opening and the at least one outlet opening of the implantable access device, wherein the inner open diameter of the at least one needle receptacle is smaller than the outer diameter of the needle introduced into the implantable access device. Usually such implantable access devices are used for one specific kind of treatment, like e.g. a hemodialysis, wherein each kind of treatment has a minimum flowrate that must be achievable. Since this minimum flowrate directly relates to the inner open diameter of the needle and the inner open diameter of the at least one passageway, the minimum outer diameter of the needle used for the specific kind of treatment is known. Thus, the inner open diameter of the at least one needle receptacle can be chosen to be smaller than the outer diameter of the smallest needle for the specific treatment but larger than the minimum inner open diameter of the smallest needle for the specific treatment.

Preferably the inner diameter of the at least one needle receptacle matches the bevel of the needle to achieve a proper sealing between the introduced needle and the at least one needle receptacle, achieve a streamlined flowpath to reduce hemolysis effects, minimize clotting zones, optimize rinsing of the at least one passageway, or so on.

Preferably the inner open diameter of the needle receptacle is large enough so that small diameter medical devices, like a guidewire, a cyto-brush, or similar devices can pass through the needle receptacle.

Since the at least one needle receptacle is arranged between the at least one inlet opening of the implantable access device and the at least one valve assembly the at least one needle receptacle prevents a penetration of the needle through the at least one valve assembly. Thus, this eliminates damages to the at least one valve assembly caused by the introduced needle.

According to a variant of the invention the at least one needle receptacle and the at least one valve assembly are built integrally, wherein the at least one needle receptacle faces the at least one inlet opening of the implantable access device.

According to a preferred variant the at least one needle receptacle is arranged movable in a longitudinal direction of the at least one passageway to actuate the at least one valve assembly. Thus, the needle introduced into the at least one inlet opening of the implantable access devices is first received by the at least one needle receptacle. By further pushing the introduced needle in the direction of the at least one passageway the at least one needle receptacle moves in the direction of the at least one passageway and thereby actuates the at least one valve assembly. Thus, the at least one valve assembly is transferred to the second, actuated operating condition by insertion of the needle into the at least one inlet opening of the implantable access device and pushing the at least one movable needle receptacle towards the at least one valve assembly, which reduces its longitudinal elongation and expands radially.

In a particularly preferred variant of the invention the at least one needle receptacle consists of a material that is harder than the material of the needle inserted into the at least one inlet opening, particularly of ceramic, hardened metal like titanium nitride, stainless steel (1NOX), high density polyethylene and other hard biocompatible non friable materials. Thereby damages caused by the insertion of the needle into the implantable access device can be significantly reduced or even eliminated.

According to a further variant of the invention the at least one valve assembly comprises at least one sealing element, wherein the at least one sealing element is radially movable relative to the longitudinal direction of the passageway. Thus, the at least one sealing element of the at least one valve assembly is responsible for sealing the passageway between the at least one inlet opening and the at least one outlet opening of the implantable access device. This at least one sealing element can be for example combined with the aforementioned at least one spring element of the at least one valve assembly. Thus, for example the at least one valve assembly comprises the at least one spring element for implementing the first and second operating condition and the at least one sealing element to implement the sealing of the at least one passageway between the at least one inlet opening and the at least one outlet opening of the implantable access device. Thus, these two functions of the at least one valve assembly are clearly separated and implemented by two different elements co-acting with each other.

In a further variant of the invention the at least one valve assembly further comprises a flexible tubing as the at least one passageway, wherein the flexible tubing is squeezed, preferably by the at least one sealing element, in the first, unactuated operating condition and uncompressed in the second, actuated operating condition. Thus, only the flexible tubing of the at least one valve assembly is in contact with the fluid flowing through the at least one passageway between the at least one inlet opening and the at least one outlet opening of the implantable access device. This further allows to create a streamlined flowpath within the at least one passageway between the at least one inlet opening and the at least one outlet opening of the implantable access device, which preferably has no discontinuities.

Preferably the at least one valve assembly comprises at least two sealing elements movable relative to each other in a radial direction relative to the longitudinal direction of the passageway to prevent a fluid flow through the at least one passageway in the first, unactuated operating condition and to permit a fluid flow through the at least one passageway in the second, actuated operating condition. By providing at least two sealing elements which are movable relative to each other in a radial direction relative to the longitudinal direction of the passageway the passageway can be opened and sealed very quickly since the at least two sealing elements move away from each other to open the at least one passageway.

In a particularly preferred embodiment the flexible tubing as the at least one valve assembly comprises at least one handle on the outer surface. The handle supports the change from the first, unactuated operating condition to the second, actuated operating condition and/or from the second, actuated operating condition to the first, unactuated operating condition. In case of a flexible tubing, e.g. made of silicone, there is a risk that the inner surfaces of the flexible tubing (partially) stick to each other during the transfer from the first, unactuated operating condition to the second, actuated operating condition. In this case the passageway is not totally opened and the fluid flow therethrough is limited. The at least one handle on the outer surface of the flexible tubing can avoid this sticking of inner surfaces.

In one variant the handle is connected to the at least one spring element which constrains the at least one valve assembly into the first, unactuated operating condition. During the transfer from the first, unactuated operating condition to the second, actuated operating condition the at least one spring element pulls at the handle of the flexible tubing in a radial direction and thereby completely opens the passageway through the valve assembly built by the flexible tubing.

In a further variant of the invention, the at least one handle on the outer surface is connected to the at least one sealing element, which is radially movable relative to the longitudinal direction of the at least one passageway/flexible tubing. By this radial movement of the at least one sealing element the at least one sealing element can pull or push the handle on the outer surface of the flexible tubing in a radial direction and thereby completely opens or closes the passageway through the valve assembly built by the flexible tubing.

According to a particularly preferred variant the at least one sealing element is C-shaped and engages the handle on the outer surface of the flexible tubing. Furthermore, the at least one sealing element can be connected to the at least spring element, which can radially move the at least one sealing element during the from the first, unactuated operating condition to the second, actuated operating condition and/or from the second, actuated operating condition to the first, unactuated operating condition.

Advantageously the flexible tubing comprises at least two handles, which are located on opposite outer surfaces of the flexible tubing. Thus, a radially outward movement of these at least two handles pulls the outer surfaces and thus also the inner surfaces of the flexible tubing apart from each other and a radially inward movement of these at least two handles pushes the outer surfaces and thus also the inner surfaces of the flexible tubing against each other.

In a variant of the invention the at least one inlet opening and the at least one outlet opening are located on opposing sides of the implantable access device, preferably on opposing sides in the longitudinal direction of the implantable access device. Thus, the at least one passageway between the at least one inlet opening and the at least one outlet opening is substantially straight. Further, thereby the housing of the implantable access device can have a streamlined or longitudinal form, with a larger longitudinal elongation than radial elongation. This is particularly preferred for implantation to reduce local stress to the skin of the human or animal body in the region where the implantable access device is actually implanted.

According to a further variant the implantable access device further comprises fixing means for retaining a needle inserted into the at least one inlet opening relative to the implantable access device. The fixing means can for example create a friction force or clamping force between the fixing means and the inserted needle. This is particularly useful during longer treatments because an accidentally retraction of the needle from the implantable access device is prevented. Further, the fixing means preferably provide means for retrieving the fixed needle, particularly by a specific movement, like a rotation or a translation, of the fixed needle. This allows an easy removal of the inserted needle, while still preventing an accidentally removal of the needle from the implantable access device. This results in more autonomy of hemodialysis patients.

In a further variant of the invention the implantable access device further comprises needle guiding means for guiding a needle to be inserted into the implantable access device towards the direction of the at least one inlet opening. Thereby a needle can be very easily inserted into the at least one inlet opening of the implantable access device. This is particularly useful for home applications, where the patient itself or a family member has to insert the needle into the implantable access device.

According to a variant the needle guiding means are channel like, preferably comprising a closing from a parabolic or U-shaped cross section towards a closed shaped like a circle, square or oval, preferably with a surface junction. Thus, the needle is first inserted into the skin of the human or animal body in the region of the parabolic or U-shaped cross section and received thereby. By further inserting the needle under the skin of the human or animal body, the needle is directed towards the closed shape, which is the at least one inlet opening of the implantable access device, by the needle guiding means.

BRIEF DESCRIPTION OF THE DRAWINGS

In the following the invention will be further explained with respect to embodiments shown in the figures, in which.

DETAILED DESCRIPTION

Figure 1:
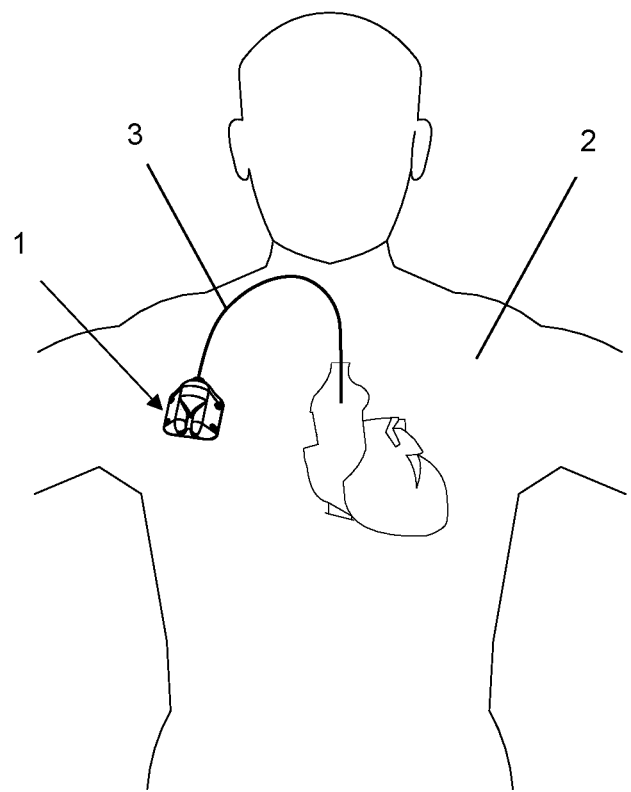
FIG. 1 shows a schematic view of the use of an implantable access device according to the invention.

FIG. 1 shows a schematic view of the use of an implantable access device 1 according to the invention. The implantable access device 1 is used for accessing the vascular system of a human or animal body 2. Therefore, the implantable access device 1 is subcutaneously implanted, for example in the chest area of the human or animal body 2, as shown in FIG. 1. The subcutaneously implanted access device 1 is connected to a subcutaneously implanted catheter 3. This subcutaneously implanted catheter 3 accesses a vessel of the vascular system of the human or animal body 2, like for example a vein or artery. The subcutaneously implanted catheter 3 is guided through the vascular system of the human or animal body 2 into right atrium of the heart. Thus, the fluids or drugs injected through the subcutaneously implanted access device 1 are rapidly distributed through the vascular system of the human or animal body 2.

The implantable access device 1 is not only suitable for chemotherapy but also for all kinds of medical treatments which require repeated access the vascular system of a human or animal body 2, like for example infusing therapeutic agents, drugs or such the like, removing body fluids, treating body fluids, injecting contrast agents and/or insertion of medical devices such as cameras, ultra-sound probes, catheters, catching devices or similar devices.

The implantable access device 1 is further particularly suitable for fluid exchange therapies like for example hemodialysis, hemofiltration, hemodiafiltration, plasmapheresis, ultrafiltration, aquafiltration, n lipid pheresis, hemoperfusion, peritoneal dialysis or the like, which usually require a high-volume fluid flow. For fluid exchange therapies two separate implantable access devices 1 or one implantable access device with two separate flow paths are necessary. One implantable access device 1 or separate flow path is connected to an artery of the vascular system of the human or animal body 2 for withdrawal of blood and the other implantable access device 1 or the other separate flow path is connected to a vein of the vascular system of the human or animal body 2 for returning the treated blood. Further, fluid exchange therapies can be conducted using a single implantable access device with a single flow path by alternatively withdrawing and returning the withdrawn blood. Therefore, special needles have been developed which support the alternating switching between withdrawing and returning blood through the implanted access device.

Figure 2:
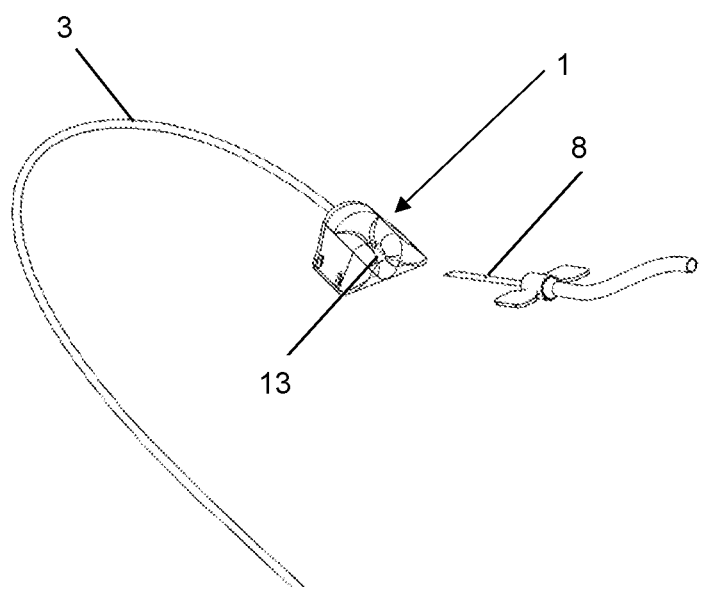
FIG. 2 shows a perspective view of an embodiment of an implantable access device according to the invention.
Figure 3:
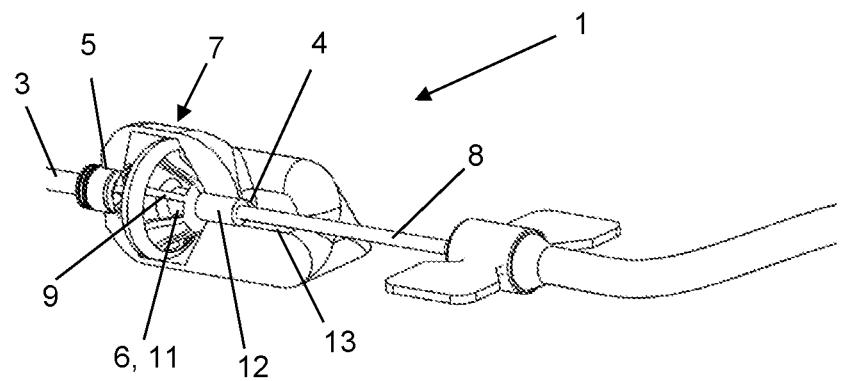
FIG. 3 shows a partially cross-sectional view of the implantable access device of FIG. 2.

FIG. 2 shows a perspective view of an exemplary embodiment of an implantable access device 1 for accessing the vascular system 3 of a human or animal body 2 and FIG. 3 shows a cross-sectional view of the implantable access device 1 from FIG. 2. The implantable access device 1 is a subcutaneously implantable access port and comprises at least one inlet opening 4, at least one outlet opening 5 and at least one passageway 6 between the at least one inlet opening 4 and the at least one outlet opening 5, as can be best seen in FIG. 3. The implantable access device 1 further comprises at least one valve assembly 7 in the at least one passageway 6, which in a first, unactuated operating condition prevents a fluid flow through the at least one passageway 6 and in a second, actuated operating condition permits a fluid flow through the at least one passageway 6.

According to the invention the at least one valve assembly 7 is in the first, unactuated operating condition longitudinally elongated and radially compressed in such a way to prevent a fluid flow through the at least one passageway 6 and in the second, actuated operating condition the at least one valve assembly 7 is longitudinally compressed and radially elongated in such a way to permit a fluid flow through the at least one passageway 6.

The implantable access device 1 according the invention, as shown in FIGS. 2 and 3, is very easy to manufacture since the at least one valve assembly 7 does not need any movable sealing parts or leaflet elements, which are complicated to manufacture. The valve assembly 7 of the implantable access device 1 only changes its longitudinal and radial dimensions from the first, unactuated operating condition to the second, actuated operating condition to open the flow-path through the streamlined passageway 6 between the at least one inlet opening 4 and the at least one outlet opening 5. By radially elongating the at least one valve assembly 7 in the second, actuated operating condition the passageway 6 is opened. The radial elongation is compensated by the longitudinal compression of the at least one valve assembly 7 in the second, actuated operating condition.

Since the valve assembly 7 radially expands in the second, actuated operating condition the valve assembly 7 opens the at least one passageway 6 between the at least one inlet opening 4 and the at least one outlet opening 5. Thus, even if a needle 8 is introduced into the at least one passageway 6 between the at least one inlet opening 4 and the at least one outlet opening 5, the at least one valve assembly 7 has already opened the at least one passageway 6 due to the radially outward movement. Thereby the risk of damaging the at least one valve assembly 7 is significantly reduced.

In a variant of the invention the at least one valve assembly 7 is arranged in the at least one passageway 6 in such a way, that the at least one valve assembly 7 is actuated by the needle 8 inserted into the at least one inlet opening 4. Therefore, the at least one valve assembly 7 is preferably arranged in the at least one passageway 6 close to the at least one inlet opening 4.

Alternatively, the at least one valve assembly 7 could also be actuated by manually applying a force through the skin of the human or animal body 2 to a special actuator, like a lever or button at the outside of the housing of the implantable access device 1, which is located on a surface directed towards the skin of the human or animal body 2. Further, the at least one valve assembly 7 could also be electronically actuated by transmitting a radio signal to a receiver of the implantable access device 1 or by transmitting electrical energy to the implantable access device 1 to feed power to a special actuator element of the at least one valve assembly 7.

In the embodiment of FIGS. 2 and 3 the at least one valve assembly 7 comprises at least one spring element 9 to constrain the at least one valve assembly 7 into the first, unactuated operating condition. By inserting the needle 8 into the at least one inlet opening 4 the at least one valve assembly 7 is actuated due to a force overcoming the spring force of the at least one spring element 9.

At least a part of the at least one spring element 9, preferably the complete at least one spring element 9, is located outside of the at least one passageway 6, so that this part of the at least one spring element 9, or the complete at least one spring element 9, does not get into contact with the fluid flowing through the at least one passageway 6.

According to an embodiment of the invention the at least one valve assembly 7 comprises at least one sealing element 10, wherein the at least one sealing element is radially movable relative to the longitudinal direction of the at least one passageway 6. Preferably the at least one valve assembly 7 comprises at least two sealing elements 10 movable relative to each other in a radial direction relative to the longitudinal direction of the at least one passageway 6 to prevent a fluid flow through the at least one passageway 6 in the first, unactuated operating condition and to permit a fluid flow through the at least one passageway 6 in the second, actuated operating condition. The at least one sealing element 10 can be for example constrained to the first, unactuated operating condition by the at least one spring element 9. Thus, only the at least one sealing element 10 is contact with the fluid flowing through the at least one passageway 6 and not the at least one spring element 9.

In a preferred embodiment of the invention the at least one valve assembly 7 further comprises a flexible tubing 11 as part of the at least one passageway 6 between the at least one inlet opening 4 and the at least one outlet opening 5. The flexible tubing is for example squeezed by the at least one sealing element 10 in the first, unactuated operating condition and uncompressed in the second, actuated operating condition.

The implantable access device 1 according to the invention can further comprise at least one needle receptacle 12 arranged in the at least one passageway 6 for receiving the needle 8 inserted into the at least one inlet opening 4, wherein the needle receptacle 12 preferably prevents a passage of the needle 8 through the needle receptacle 12. For example, the at least one needle receptacle 12 is located between the at least one inlet opening 4 of the implantable access device 1 and the at least one valve assembly 7.

The at least one needle receptacle 12 has an inner open diameter, which is part of the at least one passageway 6 between the at least one inlet opening 4 and the at least one outlet opening 5 of the implantable access device 1, wherein the inner open diameter of the at least one needle receptacle 12 is smaller than the outer diameter of the needle 8 introduced into the implantable access device 1. Usually such implantable access devices 1 are used for one specific kind of treatment, like e.g. a hemodialysis, wherein each kind of treatment has a minimum flowrate that must be achievable. Since this minimum flowrate directly relates to the inner diameter of the needle 8 and the inner diameter of the at least one passageway 6, the minimum outer diameter of the needle 8 used for the specific kind of treatment is known. Thus, the inner open diameter of the at least one needle receptacle 12 can be chosen to be smaller than the outer diameter of the smallest needle 8 for the specific treatment but larger than the minimum inner diameter of the smallest needle 8 for the specific treatment.

Preferably the inner open diameter of the needle receptacle 12 is large enough so that small diameter medical devices, like a guidewire, a cyto-brush, or similar devices can pass through the at least one needle receptacle 12.

Since the at least one needle receptacle 12 is arranged between the at least one inlet opening 4 of the implantable access device 1 and the at least one valve assembly 7 the at least one needle receptacle 12 prevents a penetration of the needle 8 through the at least one valve assembly 7. Thus, this eliminates damages to the at least one valve assembly 7 caused by the introduced needle 8.

According to a preferred embodiment of the invention the at least one needle receptacle 12 is arranged movable in a longitudinal direction of the at least one passageway 6 to actuate the at least one valve assembly 7. Thus, the needle 8 introduced into the at least one inlet opening 4 of the implantable access devices 1 is first received by the at least one needle receptacle 12. By further pushing the introduced needle 8 in the direction of the at least one passageway 6, for example to overcome the spring force of the at least one spring element 9, the at least one needle receptacle 12 moves in the direction of the at least one passageway 6 and thereby actuates the at least one valve assembly 7. Thus, the at least one valve assembly 7 is transferred to the second, actuated operating condition by insertion of the needle 8 into the at least one inlet opening 4 of the implantable access device 1 and pushing the at least one movable needle receptacle 12 towards the at least one valve assembly 7, which reduces its longitudinal elongation and expands radially.

Preferably the at least one needle receptacle 12 consist of a material that is harder than the material of the needle 8 inserted into the at least one inlet opening 4, particularly of ceramic, hardened metal like titanium nitride, stainless steel (INOX), high density polyethylene and other hard biocompatible non friable materials. Thereby damages caused by the insertion of the needle 8 into the implantable access device 1 can be significantly reduced or even eliminated.

As shown in FIGS. 2 and 3 the at least one inlet opening 4 and the at least one outlet opening 5 are located on opposing sides of the implantable access device 1, preferably on opposing sides in the longitudinal direction of the implantable access device 1. Thus, the at least one passageway 6 between the at least one inlet opening 4 and the at least one outlet opening 5 is substantially straight. Further, thereby the housing of the implantable access device 1 can have a streamlined or longitudinal form, with a larger longitudinal elongation than radial elongation. This is particularly preferred for implantation to reduce local stress to the skin of the human or animal body 2 in the region where the implantable access device 1 is actually implanted.

The implantable access device 1 can further comprises fixing means (not shown) for retaining the needle 8 inserted into the at least one inlet opening 4 relative to the implantable access device 1. The fixing means can for example create a friction force or clamping force between the fixing means and the inserted needle 8. This is particularly useful during longer treatments because an accidentally retraction of the needle 8 from the implantable access device 1 is prevented. Further, the fixing means preferably provide means for retrieving the fixed needle 8, particularly by a specific movement, like a rotation or a translation, of the fixed needle 8. This allows an easy removal of the inserted needle 8, while still preventing an accidentally removal of the needle 8 from the implantable access device 1.

As shown in FIGS. 2 and 3 the implantable access device 1 further comprises needle guiding means 13 for guiding the needle 8 to be inserted into the implantable access device 1 towards the direction of the at least one inlet opening 4. Thereby the needle 8 can be very easily inserted into the at least one inlet opening 4 of the implantable access device 1. This is particularly useful for home applications, where the patient itself or a family member has to insert the needle 8 into the implantable access device 1.

The needle guiding means 13 are for example channel like, preferably comprising a closing from a parabolic or U-shaped cross section towards a closed shaped like a circle, square or oval, preferably with a surface junction. Thus, the needle 8 is first inserted into the skin of the human or animal body 2 in the region of the parabolic or U-shaped cross section and received thereby. By further inserting the needle 8 under the skin of the human or animal body 2, the needle 8 is directed towards the closed shape, which is the at least one inlet opening 4 of the implantable access device 1, by the needle guiding means 13.

Figure 4:
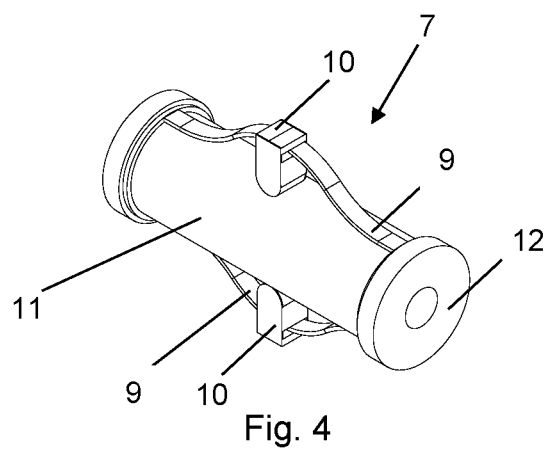
FIG. 4 shows a detailed view of a first valve assembly for an implantable access device according to the invention.
Figure 5:
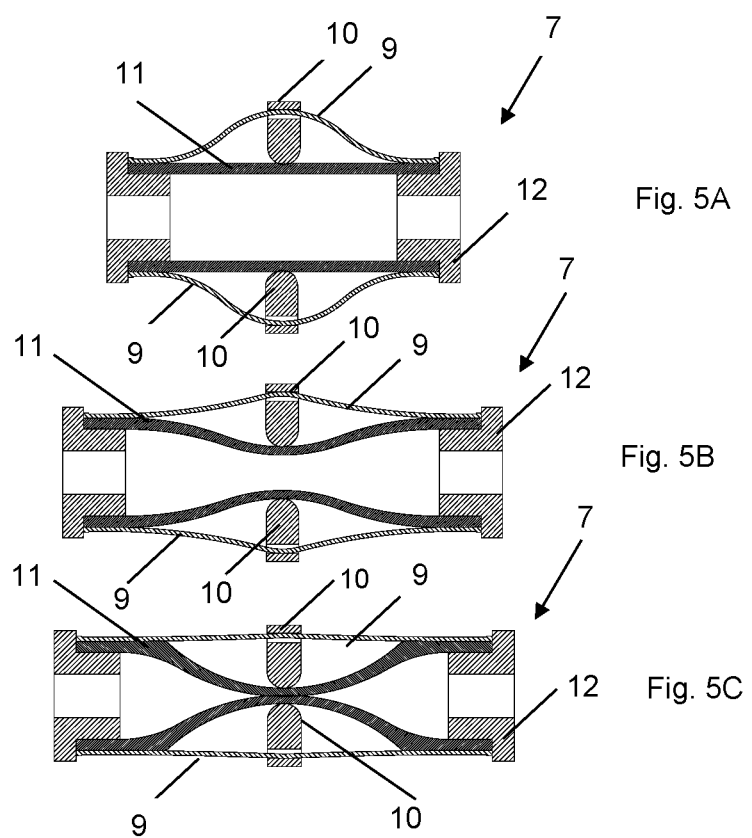
FIGS. 5A, 5B and 5C show cross-sectional views of the first valve assembly of FIG. 4 in different operating conditions.

FIG. 4 shows a detailed view of a first valve assembly 7 for an implantable access device 1 according to the invention and FIG. 5 shows cross-sectional views of the valve assembly of FIG. 4 in different operating conditions.

The valve assembly 7 shown in FIG. 4 is for the use with an implantable access device 1 according to the present invention, wherein the valve assembly 7 is arranged in the at least one passageway 6 between the at least one inlet opening 4 and the at least one outlet opening 5 of the implantable access device 1. In a first, unactuated operating condition the valve assembly 7 prevents a fluid flow through the at least one passageway 6 and in a second, actuated operating condition the valve assembly 7 permits a fluid flow through the at least one passageway 6. The valve assembly of FIG. 4 is shown in the second, actuated operating condition.

FIG. 5a shows the valve assembly 7 in the second, actuated operating condition, FIG. 5b shows the valve assembly 7 in a partly actuated operating condition and FIG. 5c shows the valve assembly 7 in the first, unactuated operating condition.

In the shown (FIGS. 4 and 5a) second, actuated operating condition the valve assembly 7 is longitudinally compressed and radially elongated in such a way to permit a fluid flow through the at least one passageway 6. In the first, unactuated operating condition, as shown in FIG. 5c, the valve assembly 7 is longitudinally elongated and radially compressed in such a way to prevent a fluid flow through the at least one passageway 7.

The shown valve assembly comprises two spring elements 9, like for example flat springs, to constrain the valve assembly into the first, unactuated operating condition in the absence of any actuation force acting on the valve assembly 7. The valve assembly 7 further comprises a flexible tubing 11 as part of the at least one passageway 6 between the at least one inlet opening 4 and the at least one outlet opening 5 of the implantable access device 1. The flexible tubing 11 is squeezed by two sealing elements 10 in the first, unactuated operating condition (see FIG. 50) and uncompressed in the second, actuated operating condition (see FIGS. 4 and 5a). The two sealing elements 10 of the valve assembly 7 are movable relative to each other in a radial direction relative to the longitudinal direction of the passageway 6. In the first, unactuated operating condition as shown in FIG. 5c the two sealing elements squeeze the flexible tubing 11 in such a way to prevent a fluid flow through the flexible tubing 11. In the second, actuated operating condition, as shown in FIGS. 4 and 5a, the two sealing elements 10 have radially moved relative to other, so that the flexible tubing is uncompressed and fluid can flow through the flexible tubing 11.

The two spring elements 9 and the two sealing elements 10 are located outside of the at least one passageway 6, which is formed by the flexible tubing 11. Thus, only the flexible tubing 11 of the valve assembly 7 is in contact with the fluid through the at least one passageway 6 and not the other parts of the valve assembly 7, like the two spring elements 9 and/or the two sealing elements 10.

The valve assembly further comprises at least one needle receptacle 12 for receiving a needle 8 inserted through the at least one inlet opening 4 towards the valve assembly 7. The needle receptacle 12 prevents a passage of the needle 8 through the needle receptacle 12 into the flexible tubing 11 of the valve assembly 7. The needle receptacle 12 consist of a material that is harder than the material of the needle 8 inserted into the at least one inlet opening 4, particularly of ceramic, hardened metal like titanium nitride, stainless steel (INOX), high density polyethylene and other hard biocompatible non friable materials.

Figure 6:
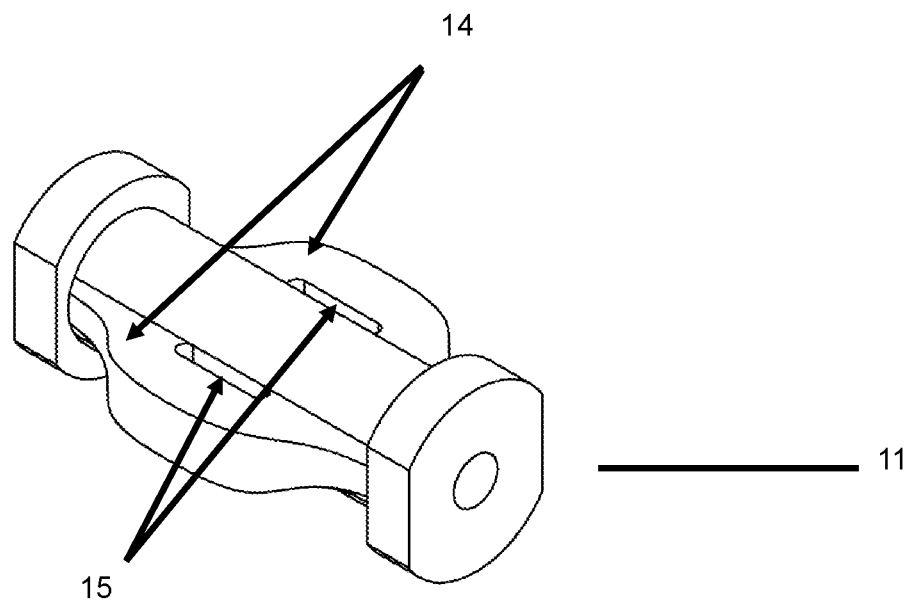
FIG. 6 shows a perspective view of a flexible tubing with at least one handle as the at least one valve assembly.

FIG. 6 shows a perspective view of a flexible tubing 11 as the at least one valve assembly 7. The flexible tubing 11 comprises in this embodiment two handles 14 on the outer surface. Between each handle 11 and an outer surface of the flexible tubing a free area 15 is located.

The two handles 14 support the change from the first, unactuated operating condition to the second, actuated operating condition and/or from the second, actuated operating condition to the first, unactuated operating condition. This is achieved by pulling and/or pushing the handles 14 in a radial direction compared to the longitudinal direction of the flexible tubing 11.

If a flexible tubing made of silicone is used, the inner surfaces of the flexible tubing at least partially stick together during a change from the first, unactuated operating condition to the second, actuated operating condition. This results in an at least partially blocked passageway 6 through the valve assembly 7, which negatively changes the flow rate. By pulling the handles 14 in a radially outward direction the outer surfaces and thus also the inner surfaces of the flexible tubing 11 are pulled apart and thereby fully opening the passageway 6 through the valve assembly 7. By pushing the handles 14 radially inwardly the outer surfaces and thus also the inner surfaces of the flexible tubing 11 are pushed against each other and thereby completely closing the passageway 6 of the valve assembly 7. Preferably the flexible tubing comprises at least two handles 14 which are located on opposite outer surfaces of the flexible tubing 11.

The free area 15 between each handle 14 and a corresponding outer surface of the flexible tubing 15 is used to connect the handle 14 to a spring element 9 or a sealing element 10, so that the spring element 8 and/or the sealing element 10 can be pushed or pulled in a radial direction compared to the longitudinal direction of the flexible tubing 11.

Figure 7:
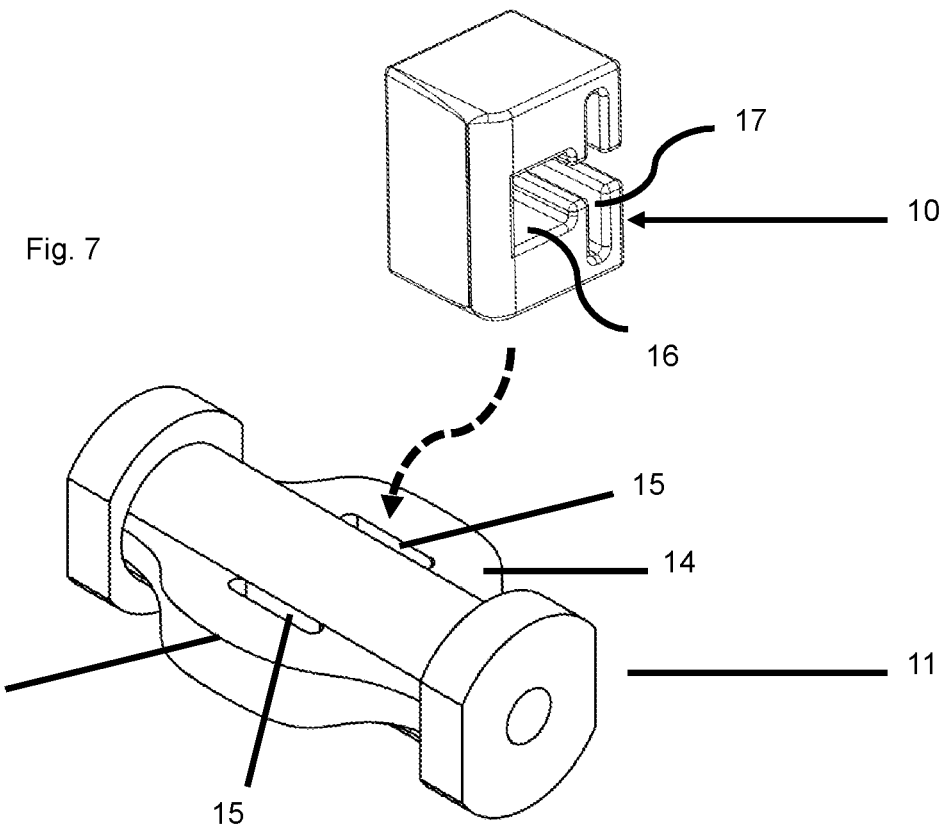
FIG. 7 shows the flexible tubing from FIG. 6 and a corresponding sealing element for grasping the handle of the flexible tubing.

FIG. 7 shows the flexible tubing 11 of FIG. 6 and a sealing element 10 designed to be connected to the handle 14 of the flexible tubing 11. The sealing element 10 is generally C-shaped and has a first recess 16 corresponding to the shape of the handle 14 of the flexible tubing 11 and a second recess 17 corresponding to the shape of the spring element 9. In the embodiment shown in FIG. 7 the handle 14 has a generally quadratic cross-section and therefore the first recess 16 is also generally quadratic. The second recess 17 is rectangularly flat and corresponds to a lamellar spring element 9.

Preferably the sealing element 10 is made at least partly of a flexible material, so that the two legs of the C-shape can be pulled apart in order connect the sealing element 10 to the handle 14 of the flexible tubing 11. However, compared to the flexible tubing 11 the sealing element 10 has a higher rigidity.

Figure 8B:
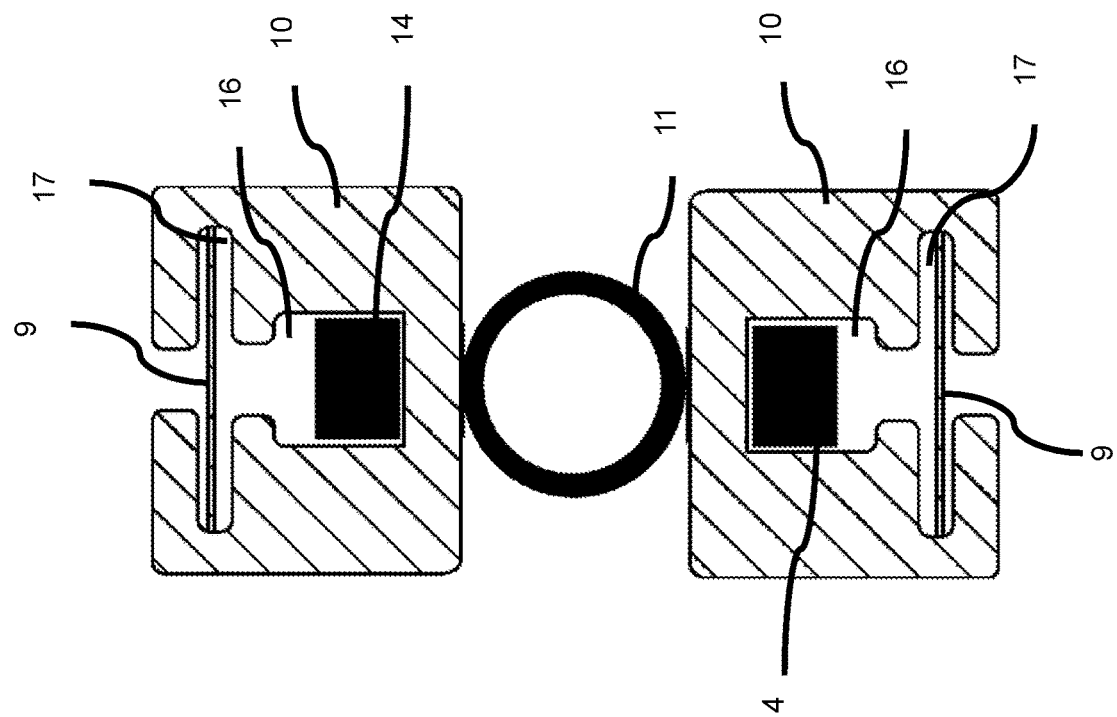
FIGS. 8A and 8B show a flexible tubing with at least one handle as the at least one valve assembly in an unactuated and an actuated operating condition.
Figure 8A:
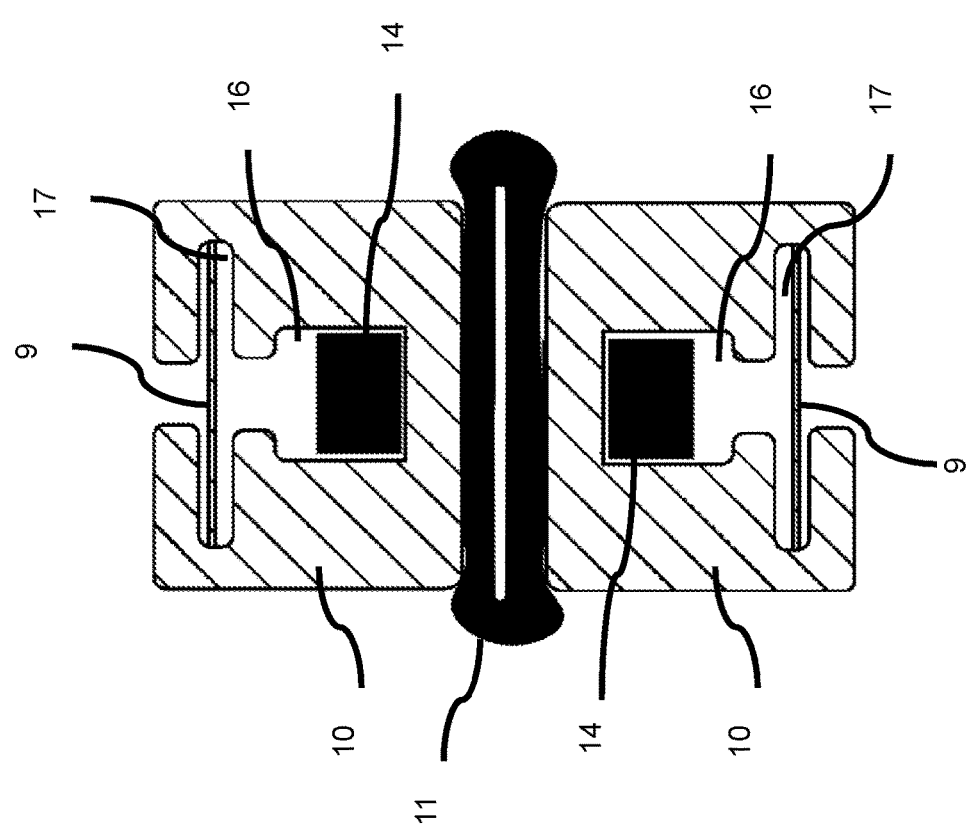

FIG. 8a shows an embodiment of the invention with a flexible tubing 11 with two handles 14, two sealing elements 10 and two lamellar spring elements 9 in a cross-sectional view in the first, unactuated operating condition. FIG. 8b shows the embodiment of FIG. 8a in the second, actuated operating condition.

In the first, unactuated operating condition the passageway through the flexible tubing 11 is closed by a radially inward movement of the sealing elements 10 caused by the lamellar spring elements 9. The generally C-shaped sealing elements 10 are arranged in the free area between each handle 14 and the outer surface of the flexible tubing 11, so that the handles 14 are arranged in the first recess 16 of the sealing elements 10. In the second recess 17 of the sealing element the lamellar spring elements 9 are arranged, which provide the radially inwardly movement of the sealing elements 10 in the first, unactuated operating condition.

In the second, actuated operating condition the inserted needle 8 applies a force to the flexible tubing 11 in the longitudinal direction of the same. This causes radially outward movement of the lamellar spring elements 8. Since these lamellar spring elements 8 are arranged in the second recess 17 of the sealing 10, the sealing elements 10 also move in radially outward direction and also apply this radially outward movement to the handles 14 of the flexible tubing 11. Thereby the inner surfaces of the flexible tubing 11 are also move in a radially outward direction and thus completely opening the passageway through the flexible tubing 11.

After the needle 8 has been removed from the implantable access device 1 the lamellar spring elements 8 again cause a radially inward movement of the sealing elements 10 and thereby closing the passageway through the flexible tubing 11.

As shown in FIGS. 8a and 8b the flexible tubing 11 comprises at least two handles 14 which are arranged on opposing sides of the flexible tubing 11.

LIST OF NUMERALS

1 Implantable access device
2 human or animal body
3 subcutaneously implanted catheter
4 inlet opening
5 outlet opening
6 passageway
7 valve assembly
8 needle
9 spring element
10 sealing element
11 flexible tubing
12 needle receptacle
13 needle guiding means
14 handle
15 free area
16 recess for handle
17 recess for spring element

What is claimed is:
1. An implantable access device for accessing the vascular system of a human or animal body, particularly a subcutaneously implantable access port, comprising:
at least one inlet opening, at least one outlet opening and at least one passageway between the at least one inlet opening and the at least one outlet opening,
at least one valve assembly disposed within the implantable access port, which in an unactuated operating condition prevents a fluid flow through the at least one passageway and in an actuated operating condition, permits the fluid flow through the at least one passageway,
wherein, in the unactuated operating condition, the at least one valve assembly, including the at least one passageway, is longitudinally elongated and radially compressed in such a way to prevent the fluid flow through the at least one passageway, wherein, in the actuated operating condition, the at least one valve assembly, including the at least one passageway, is longitudinally compressed and radially elongated in such a way to permit the fluid flow through the at least one passageway, and wherein at least a portion of the at least one passageway is provided by a flexible tubing, wherein, in the actuated operating condition, the flexible tubing is longitudinally compressed and radially elongated, and wherein, in the unactuated operating condition, the flexible tubing is longitudinally elongated and radially compressed.

2. The implantable access device according to claim 1, wherein the at least one valve assembly is arranged in the implantable access port in such a way, that the at least one valve assembly is actuated by a needle inserted into the at least one inlet opening.

3. The implantable access device according to claim 2, wherein the at least one valve assembly is arranged in the implantable access port close to the at least one inlet opening.

4. The implantable access device according to claim 1, wherein the at least one valve assembly comprises at least one spring element to constrain the at least one valve assembly into the unactuated operating condition.

5. The implantable access device according to claim 4, wherein at least a part of the at least one spring element is located outside of the at least one passageway, so that the part of the at least one spring element does not get into contact with the fluid flowing through the at least one passageway.

6. The implantable access device according to claim 1, further comprising at least one needle receptacle for receiving a needle inserted into the at least one inlet opening.

7. The implantable access device according to claim 6, wherein the at least one needle receptacle is arranged movable in a longitudinal direction of the at least one passageway to actuate the at least one valve assembly.

8. The implantable access device according to claim 6, wherein the at least one needle receptacle comprises a material that is harder than a material of the needle inserted into the at least one inlet opening.

9. The implantable access device according to claim 8, wherein the material of the at least one needle receptacle is at least one of a ceramic, a metal or a polymer.

10. The implantable access device according to claim 9, wherein the material of the at least one needle receptacle is at least one of titanium, stainless steel or polyethylene.

11. The implantable access device according to claim 6, wherein the at least one needle receptacle prevents a passage of the needle through the at least one needle receptacle.

12. The implantable access device according to claim 1, wherein the at least one valve assembly comprises at least one sealing element, wherein the at least one sealing element is radially movable relative to a longitudinal direction of the at least one passageway.

13. The implantable access device according to claim 12, wherein the at least one sealing element comprises at least two sealing elements movable relative to each other in a radial direction relative to the longitudinal direction of the at least one passageway to prevent the fluid flow through the at least one passageway in the unactuated operating condition and to permit the fluid flow through the at least one passageway in the actuated operating condition.

14. The implantable access device according to claim 1, wherein the flexible tubing comprises at least one handle on an outer surface, wherein the at least one handle supports a change from the unactuated operating condition to the actuated operating condition and/or from the actuated operating condition to the unactuated operating condition.

15. The implantable access device according to claim 14, wherein the at least one handle is connected to at least one spring element or to at least one sealing element.

16. The implantable access device according to claim 1, further comprising a needle guiding means for guiding a needle to be inserted into the implantable access device towards a direction of the inlet opening.

17. The implantable access device according to claim 16, wherein the needle guiding means are channel shaped.

18. The implantable access device according to claim 17, wherein the channel shaped needle guiding means comprise a closing from a parabolic or U-shaped cross section towards a closing shaped like a circle, square or oval.

19. The implantable access device according to claim 1, wherein the flexible tubing is compressed by at least one sealing element.

* * * * *